United States Patent
Bigham et al.

[11] Patent Number: 4,921,836
[45] Date of Patent: May 1, 1990

[54] SUBSTITUTED GLUTAMIC ACIDS

[75] Inventors: Eric C. Bigham, Chapel Hill; Stephen J. Hodson, Durham, both of N.C.

[73] Assignee: Burroughs Wellcome Co., Research Triangle Park, N.C.

[21] Appl. No.: 354,633

[22] Filed: May 17, 1989

[51] Int. Cl.$^5$ .................. C07D 239/48; A61K 37/02; A61K 31/505; C07K 5/02
[52] U.S. Cl. ........................................ 514/19; 514/17; 514/18; 514/321; 514/272; 260/998.2; 530/329; 530/330; 530/331; 530/332
[58] Field of Search .................. 260/998.2; 514/17, 18, 514/19, 272; 544/321; 530/329, 330, 331, 332

[56] References Cited
FOREIGN PATENT DOCUMENTS
0268377 5/1988 European Pat. Off. .
61/63665 4/1986 Japan .................................... 514/272
87/7801 5/1989 South Africa .

*Primary Examiner*—John M. Ford
*Attorney, Agent, or Firm*—Donald Brown

[57] ABSTRACT

The present invention provides a compound of formula (I):

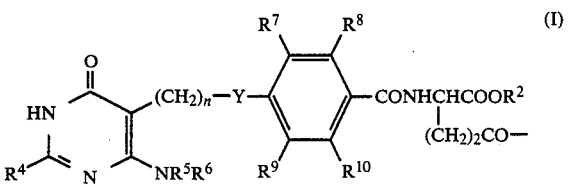

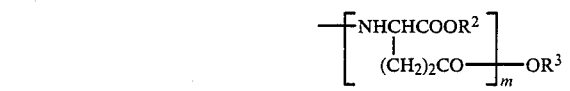

wherein Y is sulfur; $R^2$ and $R^3$ are the same or different and are hydrogen or $C_{1-4}$ alkyl; $R^4$ is $NR^{11}R^{12}$; $R^{11}$, $R^{12}$, $R^5$ and $R^6$ are the same or different and are hydrogen, $C_{1-4}$ alkyl or $C_{1-12}$ acyl; $R^7$, $R^8$, $R^9$ and $R^{10}$ are the same or different and are hydrogen, halo, $C_{1-4}$ haloalkyl, $C_{1-4}$ alkyl and $C_{1-4}$ alkoxy; and n is 2, 3, 4 or 5; m is 0 or an integer from 1 to 5; or a salt thereof, methods for the preparation of the compounds of the formula (I), intermediates in their preparations, pharmaceutical formulations containing them, and their use in the treatment of neoplastic growth.

11 Claims, No Drawings

SUBSTITUTED GLUTAMIC ACIDS

FIELD OF THE INVENTION

This invention concerns substituted glutamic acids and their composition and use. In particular, it concerns pyrimidylalkylthiobenzoyl glutamic acids, acid esters and salts, processes and intermediates for their preparation, pharmaceutical formulations containing them, and their use in medicine, particularly in the treatment of neoplastic growth.

BACKGROUND OF THE INVENTION

Pyrimidylalkylaminobenzoyl glutamic acids with anti-neoplastic activities were disclosed in European Patent Application No. 268377.

SUMMARY OF THE INVENTION

A structurally distinct class of novel substituted glutamic acids and acid esters has been discovered in which the glutamic acid or acid ester is substituted by a pyrimidylalkylthiobenzoyl chain wherein the pyrimidyl moiety is 2,4-diamino-1,6-dihydro-6-oxo-5-pyrimidinyl. The compounds of this invention have been found to possess anti-neoplastic activity in that they are able to inhibit the unregulated multiplication and proliferation of undifferentiated cells. Such activity has been demonstrated against human breast adenocarcinoma cells in a cell culture cytotoxicity test. Other aspects of this invention involve preparation of substituted glutamic acids and acid esters, their formulation into pharmaceutical compositions and their use in the treatment of neoplastic growth, e.g., leukemia, lymphoma and malignant tumors.

DETAILED DESCRIPTION OF THE INVENTION

The present invention provides a compound of formula (I):

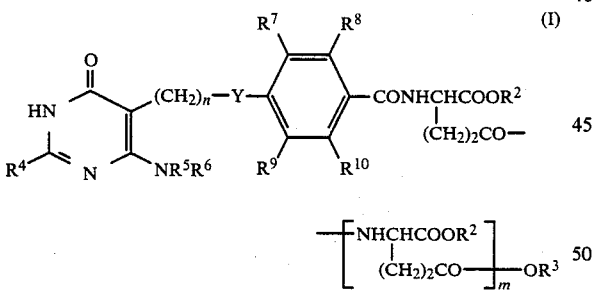

wherein Y is sulfur; $R^2$ and $R^3$ are the same or different and are hydrogen or $C_{1-4}$ alkyl; $R^4$ is $NR^{11}R^{12}$; $R^{11}$, $R^{12}$, $R^5$ and $R^6$ are the same or different and are hydrogen, $C_{1-4}$ alkyl or $C_{1-12}$ acyl; $R^7$, $R^8$, $R^9$ and $R^{10}$ are the same or different and are hydrogen, halo (e.g., chloro or fluoro), $C_{1-4}$ haloalkyl (e.g., trifluoromethyl), $C_{1-4}$ alkyl and $C_{1-4}$ alkoxy; and n is 2, 3, 4 or 5; m is 0 or an integer from 1 to 5; or a salt thereof.

Examples of $R^2$ and $R^3$, when $C_{1-4}$ alkyl, include methyl and ethyl. It is, however, preferred that $R^2$, $R^3$, $R^7$, $R^8$, $R^9$ and $R^{10}$ are hydrogen. Preferably $R^4$ and $NR^5R^6$ are both $NH_2$.

Preferably, n is 3. Suitably m is 0 to 2.

The compounds of the present invention have asymmetric carbon atoms and, therefore, can exist as optical isomers. Although all such isomers, individually and as mixtures, are included within the scope of the present invention, the L-optical isomers are preferred.

As salts of the compounds of the present invention, there are included acid addition salts derived from the pyrimidyl moiety and salts comprising an anionic species derived from a compound of formula (I), wherein one or both of $R^2$ and $R^3$ is or are hydrogen, and a cation. In both types of salts, the anti-neoplastic activity resides in the moiety derived from the compound of the invention as defined herein and the identity of the other component is of less importance although for therapeutic purposes it is, preferably, pharmaceutically acceptable to the patient. Examples of pharmaceutically acceptable acid addition salts include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycollic, gluconic, succinic and alkyl- and arylsulfonic, for example methanesulfonic and p-toluenesulfonic, acids. Examples of salts comprising an anionic species derived from a compound of formula (I), wherein one or both of $R^2$ and $R^3$ is or are hydrogen, and a cation include ammonium salts, alkali metal salts, such as sodium and potassium salts, alkaline earth salts, such as magnesium and calcium salts, and salts formed with organic bases, for example, amino salts derived from mono-, di- or tri-(lower alkyl) or (lower alkanol)amines, such as triethanolamine and diethylaminoethylamine, and salts with heterocyclic amines such as piperidine, pyridine, piperazine and morpholine. The pharmaceutically acceptable salts together with the salts which are not thus acceptable have utility in the isolation and/or the purification of the compounds of the invention, and the pharmaceutically unacceptable salts are also useful in being convertible to the pharmaceutically acceptable salts by techniques well known in the art.

The present invention also provides a process for the preparation of a compound of formula (I), as defined herein, or a salt thereof, which comprises (A) the reaction of a compound of formula (II), wherein Y, $R^5$–$R^{12}$ and n are as hereinbefore defined,

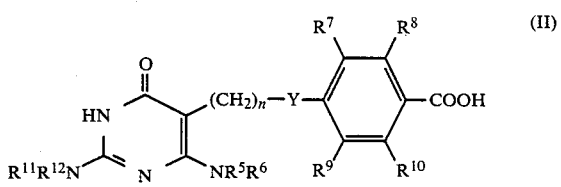

with a compound of formula (III), wherein m, $R^2$ and $R^3$ are as hereinbefore defined, and/or

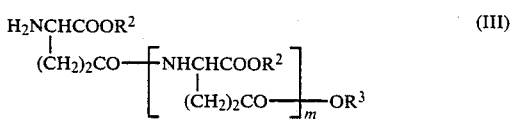

(B) interconversion of one compound of formula (I) into a different compound of formula (I), e.g. by acylation, deacylation, esterification, deesterification, or salt formation.

Compounds of formula (II) may be reacted with compounds of formula (III) to prepare compounds of formula (I) by conventional peptide coupling reactions, for example in the presence of a tertiary amine base (e.g. N-methylmorpholine), a carbodiimide (e.g. dicyclohexylcarbodiimide), and hydroxybenzotriazole or N-hydroxysuccinimide in solvents such as dimethylformamide, dimethylacetamide or methylene chloride. Alternatively, compounds of formula (II) may be coupled with compounds of formula (III) via a mixed anhydride coupling reaction, for example in the presence of a tertiary amine base and alkanoyl chloride or alkyl chloroformate in a solvent (e.g. dimethylformamide).

The deacylation of a compound of formula (I), where at least one of the groups $R^5$, $R^6$, $R^{11}$ and $R^{12}$ is $C_{1-12}$ acyl, the other groups $R^5$, $R^6$, $R^{11}$ and $R^{12}$ being the same or different and are hydrogen or $C_{1-12}$ acyl, may be carried out conventionally. Preferably, $R^5$, $R^6$, $R^{11}$ and $R^{12}$, when $C_{1-12}$ acyl, are carboxylic $C_{1-12}$ acyl. Most preferably, $R^5$, $R^6$, $R^{11}$ and $R^{12}$, when $C_{1-12}$ acyl, are the same or different and are $C_{1-12}$ carboxylic acyl, in particular $C_{1-6}$ alkanoyl, especially acetyl.

In the preferred case where $R^5$, $R^6$, $R^{11}$ and $R^{12}$, when $C_{1-12}$ acyl, are the same or different and are $C_{1-6}$ alkanoyl, the deacylation is, preferably, carried out at an elevated temperature in an alcoholic solvent, such as methanol, propanol or 2-methoxyethanol (optionally containing a small amount of 2-mercaptoethanol or dithiothreitol so as to prevent any oxidation of the resulting compound of formula (I)), in the presence of a base, such as sodium hydroxide, potassium hydroxide or ammonium hydroxide. In the event that one or both of $R^2$ and $R^3$ in the compound of formula (I) is or are $C_{1-4}$ alkyl, then the conditions preferred for deacylation are also likely to lead to deesterification. In such circumstances, the product of the deacylation is a compound of formula (I), wherein $R^2$ and $R^3$ are both hydrogen. In order, therefore, to prepare a compound of formula (I), wherein one or both of $R^2$ and $R^3$ is or are $C_{1-4}$ alkyl, the resulting compound of formula (I), wherein $R^2$ and $R^3$ are both hydrogen, is esterified as described hereinafter.

Examples of the optional conversion of $R^2$ and/or $R^3$ in the resulting compound of formula (I) into another $R^2$ and/or $R^3$ include the optional conversion of hydrogen into $C_{1-4}$ alkyl using conventional esterification reagents and conditions, for example a $C_{1-4}$ alkanol in the presence of an acid. This may be a useful optional conversion to carry out in the event that, in the preparation of a compound of formula (I), wherein one or both of $R^2$ and $R^3$ is or are $C_{1-4}$ alkyl, the compound undergoes deesterification as described hereinbefore. In such circumstances, the desired ester may be prepared from the free acid as just described.

The optional formation of a salt of a compound of formula (I) may be carried out conventionally.

Compounds of formula (III) where m is 1 to 5 may be prepared by standard peptide synthesis.

Compounds of formula (I) where m is 1 or 2 may also be prepared enzymatically from the corresponding compound of formula (I) where m is 0 by reaction with glutamic acid in the presence of a suitable enzyme, such as E. coli folylpoly-γ-glutamate synthetase.

Compounds of formula (II) may be prepared by hydrolysis of compounds of formula (IV):

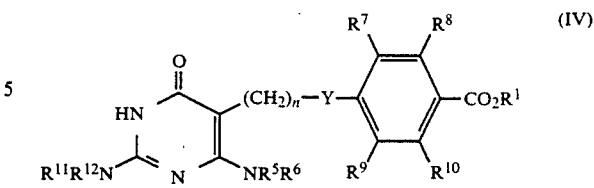

wherein Y, n, and $R^5$–$R^{12}$ are as hereinbefore defined and $R^1$ is $C_{1-4}$ alkyl, in the presence of a base, such as sodium hydroxide, in an alcoholic solvent at an elevated temperature.

Compounds of formula (IV) may be prepared by reacting compounds of formula (V):

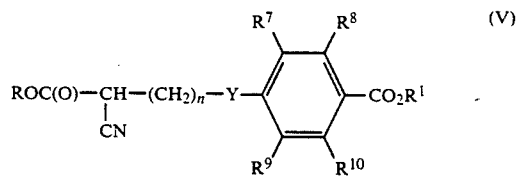

wherein Y, n, $R^1$, and $R^7$–$R^{10}$ are as hereinbefore defined and R is $C_{1-4}$ alkyl, $R^1$ and R being the same or different, with guanidine in a conventional manner, for example, in a solvent such as ethanol, in the presence of a base, such as sodium ethoxide, at an elevated temperature.

Compounds of formula (V) may be prepared by reacting a compound of formula (VI):

wherein $R^{13}$ is $C_{1-4}$ alkyl, such as ethyl, and a compound of formula (VII):

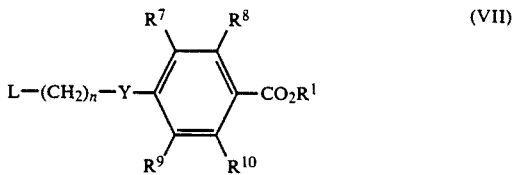

wherein $R^1$, $R^7$–$R^{10}$, Y and n are as hereinbefore defined and L is a leaving group, such as chloro, bromo, iodo, methanesulfonyloxy or tosyloxy in the presence of base.

Compounds of formula (VII) where Y is sulfur may be prepared by reacting a compound of formula (VIII):

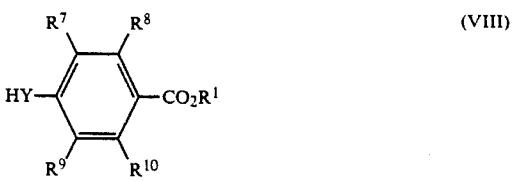

wherein Y is sulfur and $R^7$, $R^8$, $R^9$ and $R^{10}$ are as hereinbefore defined, with a compound of formula (IX):

$$L(CH_2)_nL^1 \qquad \text{IX}$$

wherein n is 2, 3, 4 or 5 and L and $L^1$ are halogen (e.g. bromo) or sulfonate (e.g. tosylate) ester, in the presence of base. L and $L^1$ may be the same or different.

The compounds of formulas (VI), (VIII) and (IX) are commercially available or may be obtained by carrying out a published process for their preparation.

While it is possible for the compounds or salts of the present invention to be administered as the raw chemical, it is preferred to present them in the form of a pharmaceutical formulation. Accordingly, the present invention further provides a pharmaceutical formulation, for medicinal application, which comprises a compound of the present invention or a pharmaceutically acceptable salt thereof, as hereinbefore defined, and a pharmaceutically acceptable carrier therefore.

The pharmaceutical formulation may optionally contain other therapeutic agents that may usefully be employed in conjunction with the compound or salt of the present invention, for example a dihydrofolate reductase inhibitor that is capable of enhancing the antineoplastic activity of the compounds and salts of the present invention. The expression "pharmaceutically acceptable" as used herein in relation to the carrier is used in the sense of being compatible with the compound or salt of the invention employed in the formulation and with any other therapeutic agent that may be present, and not being detrimental to the recipient thereof. The carrier itself may constitute one or more excipients conventionally used in the art of pharmacy that enable the compound or salt of the present invention and any other therapeutic agent that may be present, to be formulated as a pharmaceutical formulation.

The pharmaceutical formulations of the present invention include those suitable for oral, parenteral (including subcutaneous, intradermal, intramuscular and intravenous) and rectal administration although the most suitable route will probably depend upon, for example, the condition and identity of the recipient. The formulations may conveniently be presented in unit dosage form and may be prepared by any of the methods well known in the art of pharmacy. All methods include the step of bringing into association the active ingredient, i.e., the compound or salt of the present invention, with the carrier. In general, the formulations are prepared by uniformly and intimately bringing into association the active ingredient with a liquid carrier or, a finely divided solid carrier or both, and then, if necessary, forming the associated mixture into the desired formulation.

The pharmaceutical formulations of the present invention suitable for oral administration may be presented as discrete units, such as a capsule, cachet, tablet, or lozenge, each containing a predetermined amount of the active ingredient; as a powder or granules; as a solution or a suspension in an aqueous liquid or a non-aqueous liquid such as a syrup, elixir or a draught, or as an oil-in-Water liquid emulsion or a water-in-oil liquid emulsion. The formulation may also be a bolus, electuary or paste.

Generally, a tablet is the most convenient pharmaceutical formulation suitable for oral administration. A tablet may be made by compressing or molding the active ingredient with the pharmaceutically acceptable carrier. Compressed tablets may be prepared by compressing in a suitable machine the active ingredient in a free-flowing form, such as a powder or granules, in admixture with, for example, a binding agent, an inert diluent, a lubricating agent, a disintegrating agent and/or a surface active agent. Molded tablets may be prepared by molding in a suitable machine a mixture of the powdered active ingredient moistened with an inert liquid diluent. The tablets may optionally be coated or scored and may be formulated so as to provide slow or controlled release of the active ingredient.

The pharmaceutical formulations of the present invention suitable for parenteral administration include aqueous and non-aqueous sterile injection solutions which may contain, for example, an anti-oxidant, a buffer, a bacteriostat and/or a solution which renders the composition isotonic with the blood of the recipient, and aqueous and non-aqueous sterile suspensions which may contain, for example, a suspending agent and a thickening agent. The formulations may be presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

The pharmaceutical formulations of the present invention suitable for rectal administration may be presented as a suppository containing, for example, cocoa butter and polyethylene glycol.

As mentioned hereinbefore, the compounds and salts of formula (I) have anti-neoplastic activity as demonstrated in the human breast adenocarcinoma cell culture cytotoxicity test. It has thus been established that the compounds of the present invention are able to inhibit neoplastic growth. Therefore, the compounds and salts of the present invention are of use in medicine and in particular in the treatment of neoplastic growth, especially lymphocytic leukemia, lymphoma and malignant solid tumors such as melanoma, carcinoma and sarcoma in mammals. Accordingly, the present invention yet further provides a method for the treatment of susceptible malignant tumors and leukemia in an animal, e.g., a mammal, which comprises administering to the animal a therapeutically effective amount of a compound or salt of the present invention. In the alternative, there is also provided a compound or salt of the present invention for use in medicine and in particular for use in the treatment of neoplastic growth.

The present invention also provides the use of a compound of formula (I) in the manufacture of a medicament for the treatment of neoplastic growth.

The animal requiring treatment with a compound or salt of the present invention is usually a mammal, such as a human.

Particular examples of a neoplastic growth requiring treatment include lymphocytic leukemia and malignant tumors.

As mentioned hereinbefore, the antineoplastic activity of the compounds and salts of the present invention may be enhanced by a dihydrofolate reductase inhibitor, for example, 2,4-diamino-6-(2,5-dimethoxybenzyl)-5-methylpyrido[2,3-d-]pyrimidine hydrochloride. Therefore, it may be advantageous to employ with the compounds and salts of the present invention a dihydrofolate reductase inhibitor in the treatment of neoplastic growth.

The route by which the compound or salt of the present invention is administered to the animal may be oral, parenteral (including subcutaneous, intradermal, intramuscular, intravenous) or rectal. If the compound or salt is presented in the form of a pharmaceutical formulation, which, as mentioned hereinbefore, is preferred, then the actual formulation employed will of course depend on the route of administration elected by the physician or veterinarian. For example, if oral administration is preferred, then the pharmaceutical formulation employed is one which is suitable for such a route.

A therapeutically effective amount of a compound or salt of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of the present invention for the treatment of neoplastic growth, in particular lymphocytic leukemia, lymphoma or malignant tumors, such as melanoma, carcinoma and sarcoma, will generally be in the range of 0.5 to 600 mg/kg body weight of recipient (mammal) per day and more usually in the range of about 2.5 to about 100 mg/kg body weight per day. Thus, for a 70 kg adult human, the actual amount per day would usually be from about 22.5 to about 900 mg and this amount may be given in a single dose per day or more usually in a number (such as two, three, four, five or six) of sub-doses per day such that the total daily dose is the same. An effective amount of a salt of the present invention may be determined as a proportion of the effective amount of the compound per se.

The treatment of neoplastic growth with a compound of the present invention may at times require the administration to the animal of an antidote or rescue agent. Particular examples of such agents include leucovorin, hypoxanthine and 5-aminoimidazole-4-carboxamide ribonucleotide (AICAR), although leucovorin is the most preferred.

The following examples and biological data are provided in illustration of the present invention and should not be construed as in any way constituting a limitation thereof.

Example 1

Preparation of N-[4-[[3-(2,4-Diamino-1,6-dihydro-6-oxo-5pyrimidinyl)propyl]thio]benzoyl]-L-glutamic acid

1A. Ethyl 4-[(3-bromopropyl)thio]benzoate

Diethyl 4,4-Dithiobisbenzoate (Kim, Y. H. et al., *J. Med. Chem.*, 18. 776–80(1975)) (11.35 g, 31.3 mmoles) was dissolved in ethanol (350 mL) and treated with sodium borohydride (2.4 g, 63.4 mmoles). After 20 minutes, the solution was added to 1,3-dibromopropane (32 g, 158 mmoles) in ethanol (200 mL) and the mixture stirred for 18 hours. The mixture was evaporated in vacuo to a viscous residue, and chromatographed (700 g silica, 1:1 hexane/dichloromethane) to give 6.01 g (32%) of compound 1A as a colorless oil. NMR (DMSO-$d_6$) $\delta$1.3 (t, 3H CH$_3$ of ester), 2.1 (m, 2H, CH$_2$—CH$_2$CH$_2$), 3.15 (t, 2H, CH$_2$—S), 3.6 (t, 2H CH$_2$—Br), 4.28 (q, 2H, CH$_2$ of ester, 7.4 (d, 2H, benzoate H's ortho to sulfur), 7.85 (d, 2H, benzoate H's ortho to carbonyl). Compound 1A was used in the next reaction without further purification.

1B. Ethyl 4-[(4-cyano-5-ethoxy-5-oxopentyl)thio]benzoate

Ethylcyanoacetate (6.30 g, 55.7 mmoles) was added to a solution of sodium ethoxide (50 mmoles) in ethanol (25 mL) and refluxed 15 minutes. After cooling, the mixture was treated with bromide, 1A, (7.68 g, 25.3 mmoles) as a solution in ethanol (25 mL) and refluxed for 6 hours. The mixture was filtered, and the filtrate was treated with acetic acid to pH 7.0 and was evaporated to a viscous residue. The residue was partitioned between water (50 mL) and ether (50 mL), and the ether phase collected. The aqueous phase was washed with 4 volumes (50 mL) of ether, and the combined ether fractions were dried (CaSO$_4$) and filtered. The filtrate was evaporated in vacuo, and the residue chromatographed (400 g silica, 3:1 hexane/ethyl acetate) to yield 6.06 g (70%) of the title compound, 1B, as a pale yellow oil. NMR (DMSO-$d_6$) $\delta$1.17 (t, 3H, CH$_3$ of benzoate ether), 1.7 (m, 2H, CH$_2$CH$_2$—CH$_2$), 1.95 (m, 2H, CH$_2$—CH$_2$CH$_2$—S), 1.28 (t, 3H, CH$_3$ of acetate ester), 3.1 (m, 2H, CH$_2$—S), 4.15 (m, 1H, CH), 4.15 (q, 2H, CH$_2$ of benzoate ester), 4.28 (q, 2H, CH$_2$ of acetate ester), 7.4 (d, 2H, benzoate H's ortho to S), 7.85 (d, 2H, benzoate H's ortho to carbonyl). Compound 1B was used in the next reaction without further purification.

1C. Ethyl 4-[[3-(2,4-diamino-1,6-dihydro-6-oxo-5-pyrimidinyl)propyl]thio]benzoate Dry guanidine hydrochloride (3.43 g, 35.9 mmoles) was added to a solution of sodium ethoxide 53.5 mmoles) in ethanol (25 mL), and the mixture was treated with 1B (6.00 g, 17.9 mmoles) as a solution in ethanol (25 mL) and refluxed for 5 hours. After cooling, the pH was adjusted to 7.0 with acetic acid, and the mixture was evaporated to a viscous residue in vacuo. The residue was treated with water (70 mL) and was filtered to give an off white solid, which was washed with 3 volumes (30 mL) of water and 3 volumes (30 mL) of ether and was dried in vacuo to give crude product title compound, 1C, (5.96 g, 95%) as a white solid. NMR (DMSO-d6) $\delta$1.3 (t, 3H, CH$_3$ of ester), 1.65 ( m, 2H, CH$_2$—CH$_2$—CH$_2$), 2.3 (t, 2H, CH$_2$—CH$_2$—CH$_2$—S), 2.95 (m, 2H, CH$_2$—S), 4.3 (q, 2H, CH$_2$ of ester), 5.7 (br s, 2H, NH$_2$), 5.95 (br s, 2H, NH$_2$), 7.3 (d, 2H) (benzoate H's ortho to sulfur), 7.85 (d, 1H, 7.95 (d, 1H), 9.8 (br s, 1H, ring NH). The aromatic region of the NMR spectrum indicated slight impurities; compound 1C was used in the next reaction without further purification.

1D. 4-[[3-(2,4-Diamino-1,6-dihydro-6-oxo-5-pyrimidinyl)propl]thio]benzoic acid Ester 1C (5.95 g, 17.1 mmoles) was treated with 600 mL of 1:1 ethanol/1.0 N sodium hydroxide (V/V) and heated to 60° C. for 5 hours. After cooling, the solution was treated with concentrated hydrochloric acid to pH 3.5 and was filtered. The filtrate was reduced to 300 mL volume and was refiltered to give an off white solid, which was washed with 3 volumes (20 mL) of water. The solid was dissolved in 0.1 N sodium hydroxide (200 mL) and was re-acidified to pH 3.5 with concentrated hydrochloric acid. Filtration gave a white solid which was washed with 3 volumes (50 mL) of water and dried in vacuo at 50° C. to give 3.36 g (61%) of acid, 1D, as a white solid. Anal: $C_{14}H_{16}N_4O_3S$: C, 52.49; H, 5.03; N, 17.49; S, 10.00. Found: C, 52.55; H, 5.07; N, 17.40; S, 10.08. NMR (DMSO-d$_6$) δ1.6 (m, 2H, CH$_2$CH$_2$CH$_2$), 2.3 (t, 2H, CH$_2$—CH$_2$CH$_2$—S), 2.95 (t, 2H, CH$_2$—S), 6.1 (br s, CH, NH$_2$), 6.5 (br s, 2H, NH$_2$), 7.3 (d, 2H, benzoate H's ortho to sulfur), 7.8 (d, 2H, benzoate H's ortho to carbonyl), 9.9 (br s, NH). MS (CI) M/305 (M+1) 167 (m-OPhCO$_2$H) 139 (H$_2$OPhCO$_2$H+).

1E. Diethyl N-[4-[[3-(2,4-diamino-1,6-dihydro-6-oxo-5-pyrimidinyl)propyl]thio]benzoyl]-L-glutamate A sample of compound 1D (1.05 g, 3.27 mmoles) was dissolved in dry dimethylformamide (20 mL) and treated with 1-hydroxybenzotriazole (0.66 g, 4.88 mmoles) and dicyclohexylcarbodiimide (1.00 g, 4.84 mmoles) and the mixture stirred for 15 minutes. A suspension of diethyl L-glutamate hydrochloride (1.17 g, 4.88 mmoles) and triethylamine (0.49 g, 4.84 mmoles) in dimethylformamide (5 mL) was added and the mixture stirred for 20 hours. The addition of dicyclohexylcarbodiimide and diethyl glutamate was repeated and stirring continued for an additional 20 hours. The mixture was reduced in vacuo to dryness and the residue and treated with dichloromethane (50 mL) and methanol (10 mL) and filtered. The filtrate was evaporated onto flash silica (30 g) and chromatographed through 250 g of flash silica in 10:1 ethyl acetate/methanol to yield the title compound, 1E, (0.85 g, 53%) as a straw colored glass. NMR (DMSO-d$_6$)δ1.15 (2 triplets, 6H, CH$_3$'s of ethyl esters) 1.65 (m 2H, CH$_2$—CH$_2$—CH$_2$), 2.1 (m, 2H, CH$_2$ α to methine), 2.3 (t, 2H, CH$_2$—CH$_2$CH$_2$—S—), 2.4 (t, 2H, CH$_2$—CO$_2$Et), 3.0 (m, 2H, —CH$_2$—S), 4.05 (m, 4H, CH$_2$'s of ethyl esters), 4.4 (m, 1H, CH), 5.7 (s, 2H, NH$_2$), 5.9 (s, 2H, NH$_2$), 7.3 (d, 2H, phenyl H's ortho to sulfur), 7.8 (d, 2H, phenyl H's ortho to carbonyl), 8.65 (d, 1H, glutamate NH), 9.75 (s, 1H, pyrimidine NH). A small amount of an impurity with singlets at δ1.95, 3.8 and 8.3 was also present. Compound 1E used without further purification in the next reaction.

1F. N-[4-[[3-(2,4-Diamino-1,6-dihydro-6-oxo-5-pyrimidinyl)propyl]thio]benzoyl]-L-glutamic acid A sample of compound 1E (0.50 g, 0.99 mmole) was stirred at 50° C. in 0.1N NaOH (18 mL) for 2 hours. The pH was adjusted to 8.0 with 1.0 N HCl and the mixture evaporated to dryness in vacuo. The resulting solid was dissolved in a minimum of ethanol/water (35% ethanol v/v) and chromatographed in 5 injections on a Regis C$_{18}$ 2.1 cm×50 cm, 10 micron, preparative reverse phase column. The combined fractions were reduced in vacuo to 5 mL volume and acidified with concentrated HCl to pH 3.0. Filtration gave a white solid which was dried in vacuo at 50° C. to yield the title compound, 1F, (0.185 g, 41%) as a white powder. Anal: $C_{19}H_{23}N_5O_6S.3/2$ H$_2$O: C, 47.89; H, 5.48; N, 14.70. Found: C, 47.99; H, 5.51; N, 14.61. NMR (DMSO-d$_6$) δ1.6 (t, 2H, CH$_2$—CH$_2$—CH$_2$), 2.0 (m, 2H, —CH$_2$—CH$_2$—CO$_2$H), 2.35 (m, 4H, CH$_2$—CH$_2$—CH$_2$—S and CH$_2$—CO$_2$H), 2.95 (t, 2H, —CH$_2$—S), 4.35 (m, 1H, methine), 5.8 (br, 2H, NH$_2$), 6.1 (br, 2H, NH$_2$), 7.3 (d, 2H, phenyl H's ortho to sulfur), 7.75 (d, 2H, phenyl H's ortho to carbonyl), 8.55 (d, 1H, glutamic acid NH), 9.9 (br, 1H, pyrimidine NH), 12.35 (br, 2H, CO$_2$ H's).

Chemotherapeutic Data

Cell Culture Method for Evaluation of Compounds as Antitumor Agents

Cells and Medium: MCF-7 breast adenocarcinoma cells, obtained from the American Type Culture Collection (ATCC) are grown in RPMI 1640 medium supplemented with 10 nM calcium leucovorin instead of folic acid as the folate source, 10% dialyzed fetal calf serum, penicillin, streptomycin and sodium pyruvate (110 μg/ml).

Cytotoxicity Assay: Cells are seeded into 96 well plates using a Perkin Elmer Pro/pette. MCF-7 cells are seeded at 15,000 cells per well in 150 μl of medium. Prior to the addition of drugs, cultures were incubated for 24 hours at 37° C. Compounds were added at 2x concentration in 150 μl of medium and each concentration was assayed in triplicate. Cultures were incubated for 72 hours in a 37° humidified incubator at 5% CO$_2$. Inhibition of cell growth was measured using the MTT dye reduction assay.

MTT Dye Reduction Assay: Cell dilutions for a standard curve were prepared from a 72 hour log-phase culture. Serial dilutions were seeded in triplicate in 96 well plates and incubated at 37 for 1 hour. MTT (3-(4,5-dimethylthiazol-2-yl)-2,5-diphenyltetrazolium bromide) was dissolved in phosphate buffered saline at 5 mg/ml and sonicated for 30 seconds. Using the Perkin Elmer Pro/pette, 200 μl of medium was removed and 100 μl of MTT added to the wells of the standard curve and test plates. Suspension cultures were spun for 5 minutes at 1000 rpm before removing medium from the wells. Plates were incubated for 1 hour at 37° on a platform shaker. Following this incubation, 100 μl of medium was removed from the wells and 100 μl of dimethylsulfoxide added to each well. The plates were sonicated for approximately 10 seconds to solubilize the precipitated formazan dye. The absorbance of each well was measured using a Titertek Multiskan MC microtiter plate reader at 570 nm with a reference wavelength of 750 nm.

The compound of Examples 1F, was found to be active in inhibiting the growth of MCF-7 cells.

| Anti-tumor Activity Human Breast Adenocarcinoma Cells | |
|---|---|
| Compound of Example No. | IC$_{50}$ (nM) |
| 1F | 23 |

I claim:
1. A compound of formula (I):

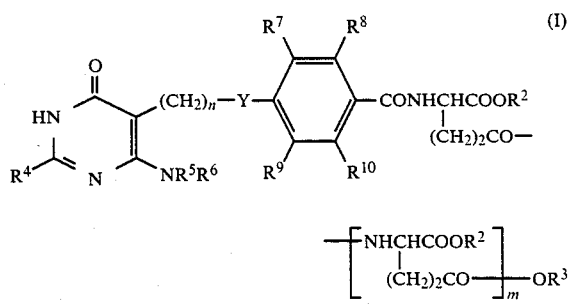

wherein

Y is sulfur; $R^2$ and $R^3$ are the same or different and are hydrogen or $C_{1-4}$ alkyl; $R^4$ is $NR^{11}R^{12}$; $R^{11}$, $R^{12}$, $R^5$ and $R^6$ are the same or different and are hydrogen, $C_{1-4}$ alkyl or $C_{1-6}$ acyl; $R^7$, $R^8$, $R^9$ and $R^{10}$ are the same or different and are hydrogen, halo, $C_{1-4}$ haloalkyl, $C_{1-4}$ alkyl and $C_{1-4}$ alkoxy; and n is 2, 3, 4 or 5; m is 0 or an integer from 1 to 5; or a salt thereof.

2. A compound according to claim 1 wherein $R^4$ and $NR^5R^6$ are both $NH_2$.

3. A compound according to claim 1 wherein $R^2$, $R^3$, $R^7$, $R^8$, $R^9$ and $R^{10}$ are all hydrogen.

4. A compound according to claim 1 wherein n is 2 or 3.

5. A compound according to claim 1 wherein m is 0.

6. The compound
N-[4-[[3-(2,4-diamino-1,6-dihydro-6-oxo-5-pyrimidinyl)propyl]thio]benzoyl]-L-glutamic acid.

7. A pharmaceutically acceptable salt of N-[4-[[3-(2,4-diamino-1,6-dihydro-6-oxo-5-pyrimidinyl)propyl]thio]benzoyl]-L-glutamic acid.

8. A pharmaceutical composition comprising the compound of claim 6 and a pharmaceutically acceptable carrier therefor.

9. A pharmaceutical composition comprising the salt of claim 7 and a pharmaceutically acceptable carrier therefor.

10. A pharmaceutical formulation which comprises a compound according to claim 1 or a pharmaceutically acceptable salt thereof and a pharmaceutically acceptable carrier therefor.

11. A method for the treatment of leukemia and malignant tumors in an animal which comprises administering to the animal a therapeutically effective amount of a compound according to claim 1 or a pharmaceutically acceptable salt thereof.

* * * * *